(12) United States Patent
Cropper et al.

(10) Patent No.: US 8,631,991 B2
(45) Date of Patent: Jan. 21, 2014

(54) SURGICAL INSTRUMENT

(75) Inventors: Michael S. Cropper, Edgewood, KY (US); Sean P. Conlon, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1169 days.

(21) Appl. No.: 11/755,430

(22) Filed: May 30, 2007

(65) Prior Publication Data
US 2008/0296344 A1 Dec. 4, 2008

(51) Int. Cl.
*A61B 17/068* (2006.01)

(52) U.S. Cl.
USPC ........................................ 227/176.1; 227/19

(58) Field of Classification Search
USPC ............... 227/176.1, 179.1, 19; 606/139, 205
See application file for complete search history.

(56) References Cited

U.S. PATENT DOCUMENTS

| | | | | |
|---|---|---|---|---|
| 3,954,108 | A | * | 5/1976 | Davis ............................ 606/142 |
| 4,014,492 | A | | 3/1977 | Rothfuss |
| 4,043,504 | A | | 8/1977 | Hueil et al. |
| 4,265,226 | A | | 5/1981 | Cassimally |
| 4,375,866 | A | | 3/1983 | Giersch |
| 4,399,810 | A | | 8/1983 | Samuels et al. |
| 4,407,286 | A | | 10/1983 | Noiles et al. |
| 4,550,715 | A | * | 11/1985 | Santangelo et al. .......... 600/114 |
| 4,607,638 | A | | 8/1986 | Crainich |
| 4,759,348 | A | * | 7/1988 | Cawood ........................ 600/102 |
| 4,841,888 | A | | 6/1989 | Mills et al. |
| 5,037,021 | A | | 8/1991 | Mills et al. |
| 5,174,487 | A | | 12/1992 | Rothfuss et al. |
| 5,395,030 | A | * | 3/1995 | Kuramoto et al. ......... 227/179.1 |
| 5,571,116 | A | | 11/1996 | Bolanos et al. |
| 5,588,581 | A | | 12/1996 | Conlon et al. |
| 5,634,584 | A | * | 6/1997 | Okorocha et al. .......... 227/176.1 |
| 5,662,662 | A | * | 9/1997 | Bishop et al. ................. 606/143 |
| 5,897,562 | A | | 4/1999 | Bolanos et al. |
| 6,206,823 | B1 | * | 3/2001 | Kolata et al. .................. 600/129 |
| 6,494,888 | B1 | | 12/2002 | Laufer et al. |
| 6,663,639 | B1 | | 12/2003 | Laufer et al. |
| 6,755,338 | B2 | * | 6/2004 | Hahnen et al. ............. 227/175.1 |
| 6,773,441 | B1 | | 8/2004 | Laufer et al. |
| 7,083,617 | B2 | * | 8/2006 | Kortenbach et al. ............ 606/46 |

FOREIGN PATENT DOCUMENTS

| | | |
|---|---|---|
| WO | WO 01/62161 | 8/2001 |
| WO | WO 02/060328 | 8/2002 |
| WO | WO 02/094341 | 11/2002 |
| WO | WO 2006/027014 | 3/2006 |

* cited by examiner

*Primary Examiner* — Alexandra Elve
*Assistant Examiner* — Nathaniel Chukwurah
(74) *Attorney, Agent, or Firm* — Welshman Flaxman & Gitler LLC

(57) ABSTRACT

A surgical instrument for fastening tissue with a staple. The instrument includes a cartridge adapted for containing the staple. The cartridge includes a mechanism adapted to selectively advance the staple toward a forward end of the cartridge so the ends of the staple protrude from the cartridge and to selectively close the staple. The cartridge includes a mount connected to the cartridge and adapted for mounting the cartridge to an end of an endoscope. The cartridge includes a linkage connected to the cartridge for actuating the mechanism to advance and close the staple and a remote actuator connected to the linkage a predetermined distance from the cartridge for actuating the mechanism from a position remote from the cartridge.

10 Claims, 3 Drawing Sheets

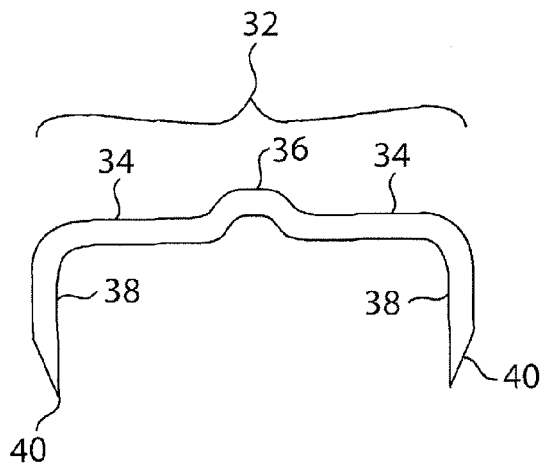
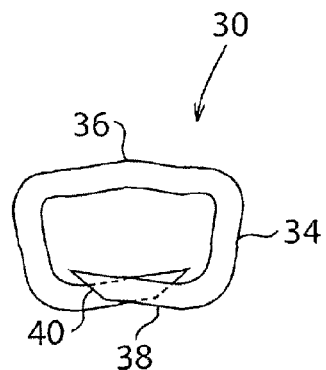
FIG. 2        FIG. 3
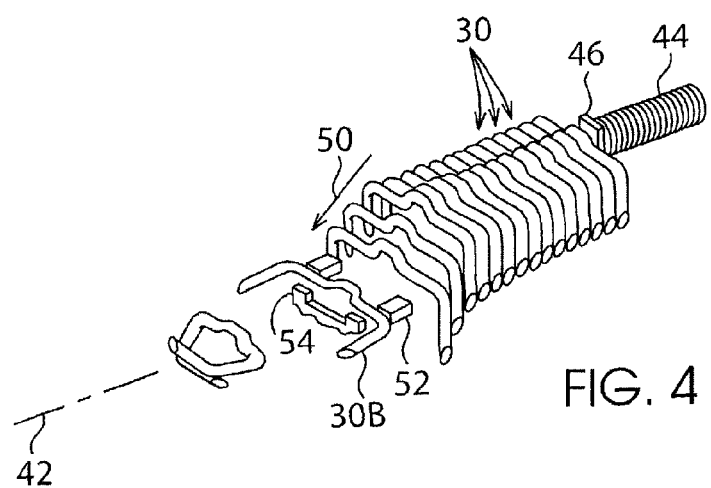
FIG. 4

SURGICAL INSTRUMENT

BACKGROUND

This invention generally relates generally to surgical instruments and more particularly to staplers used in endoscopic procedures.

A variety of designs have been commercialized or proposed for instruments having an end effector for engaging tissue during surgery and applying a fastener to the tissue. Such instruments typically have a handle for actuating the instrument. The instrument may also include parts that pivot and/or rotate to facilitate using the instrument in various orientations.

Some conventional endoscopic instruments include an operable end effector such as a staple applying cartridge for engaging the tissue in a certain way. In some of these conventional endoscopic instruments, the end effectors mount on a rigid, straight shaft of the instrument so the end effectors extend from the end of the shaft generally parallel to the shaft. Depending on the surgical procedure being performed, it is sometimes desirable to provide an end effector assembly that can be easily bent relative to the longitudinal axis of the shaft. These movements permit the surgeon to engage the tissue more easily in some situations. For example, when a staple is applied to certain hollow internal organs such the stomach, a rigid shaft cannot be used without making incisions in the patient to access the stomach. A flexible delivery system would enable the stapler to be introduced into the stomach of the patient through the esophagus. In spite of the fact that some procedures require the instrument be flexible to reach a particular area inside the patient where the procedure is being performed, most conventional endoscopic stapling devices have rigid shafts. As a result the complexity and duration of the surgical procedures may be increased, thereby increasing recover times and complications.

BRIEF SUMMARY

The present invention relates to a surgical instrument for fastening tissue with a staple. The staple is deformable from an open configuration in which tissue is initially engaged by ends of the staple to a fastened configuration in which the ends of the staple are moved toward each other so the staple closes around the tissue thereby fastening the tissue. The instrument comprises a cartridge adapted for containing the staple. The cartridge includes a mechanism adapted to selectively advance the staple toward a forward end of the cartridge so the ends of the staple protrude from the cartridge and to selectively close the staple. The instrument further includes a mount connected to the cartridge and adapted for mounting the cartridge to an end of an endoscope laterally offset from a tip of the endoscope so tissue can be viewed through the endoscope when fastened. In addition, the instrument comprises a linkage connected to the cartridge for actuating the mechanism to advance and close the staple and a remote actuator connected to the linkage a predetermined distance from the cartridge for actuating the mechanism from a position remote from the cartridge.

In another aspect of the present invention, a surgical instrument comprises a cartridge adapted for containing the staple. The cartridge includes a mechanism adapted to selectively advance the staple toward a forward end of the cartridge so the ends of the staple protrude from the cartridge and to selectively close the staple. The instrument also includes a flexible shaft connected to the cartridge for positioning the cartridge in the patient. Still further, the instrument includes a linkage connected to the cartridge and extending along the shaft for actuating the mechanism to advance and close the staple. The instrument comprises a remote actuator connected to the linkage a predetermined distance from the cartridge for actuating the mechanism from a position remote from the cartridge.

Other aspects of the present invention will be in part apparent and in part pointed out hereinafter.

BRIEF DESCRIPTION OF THE DRAWINGS

FIG. 2 is a front elevation of an undeformed staple used in a stapler of the first embodiment;

FIG. 3 is a front elevation of the staple of FIG. 2 after being deformed;

FIG. 4 is a schematic perspective of a series of staples and a portion of a cartridge of a stapler.

Corresponding reference characters indicate corresponding parts throughout the several views of the drawings.

DETAILED DESCRIPTION

Figure 1:
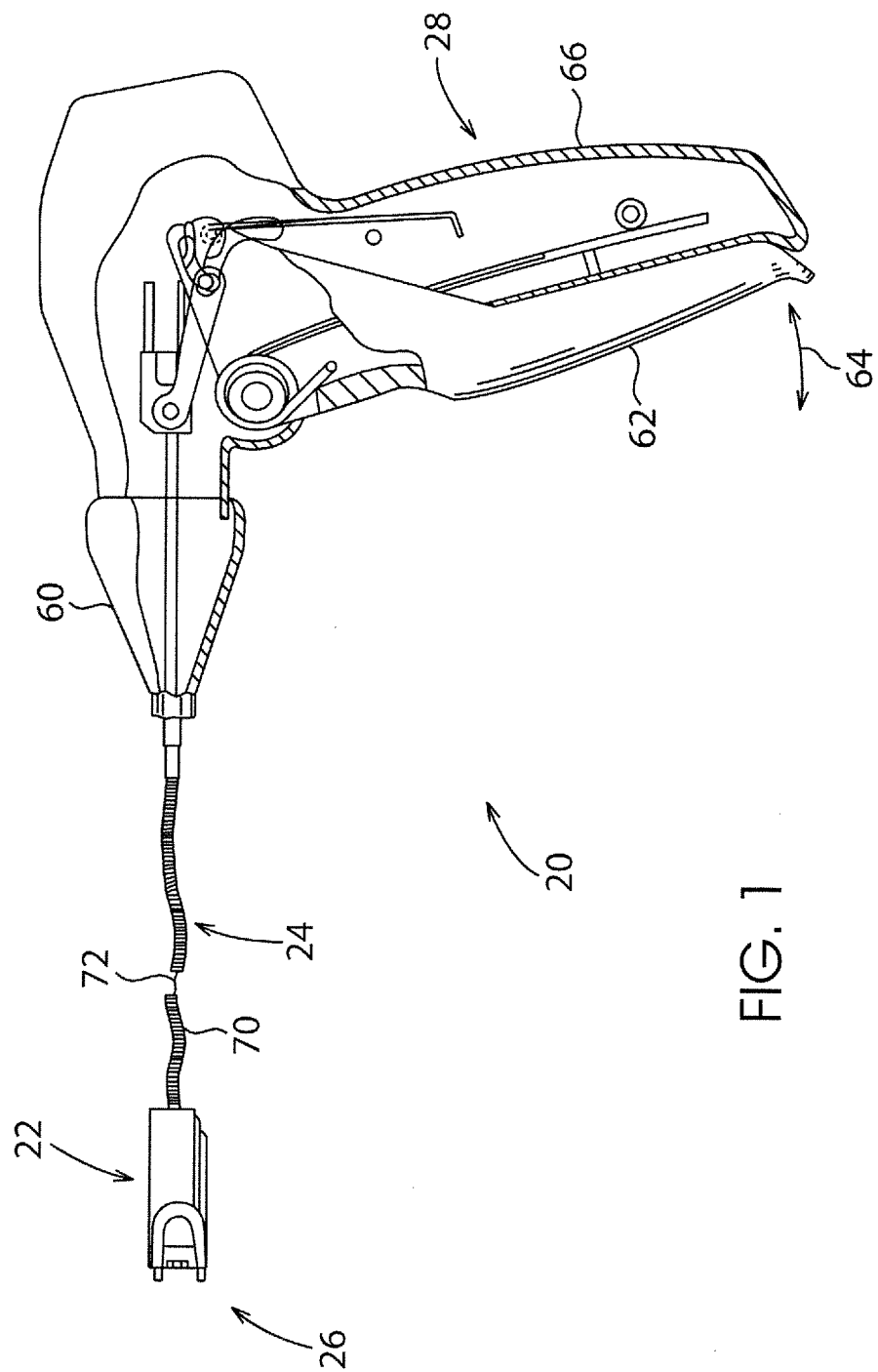
FIG. 1 is a side elevation of a endoscopic surgical stapler in partial section of a first embodiment of the present invention.

Referring now to the drawings and in particular FIG. 1, one embodiment of an endoscopic surgical stapler is designated in its entirety by the reference numeral 20. The stapler 20 is a surgical instrument including a staple cartridge (generally designated by 22) mounted on a flexible shaft (generally designated by 24) at a working end (generally designated by 26) of the stapler. A manipulator handle (generally designated by 28) is attached to the shaft 24 opposite the cartridge 22 for manipulating the cartridge into position and actuating the cartridge to apply a staple once the cartridge is in position. The cartridge 22 is adapted to hold a supply of staples, each staple generally designated by 30, (FIG. 2) and to individually apply the staple to tissue (not shown).

Usually, the staples 30 are applied to hold two portions of tissue together, but if desired the staples 30 may be used to attach a non-tissue element (e.g., a medical implant or surgical mesh) to one or more portions of tissue. Although the staple 30 may be made from other suitable materials without departing from the scope of the present invention, in some embodiments the staple is made from titanium, stainless steel, or other metals used in surgical applications. In appropriate applications, the staple 30 may be made from non-metallic materials, including synthetic polymers. Each staple 30 has a transverse member or crown 32 having opposite end portions 34 joined by a central portion 36. Prior to being deformed in use, the central portion 36 of the staple 30 is vertically offset from the end portions 34. Each crown end portion 34 joins an upper end of a leg 38 oriented generally perpendicular to the crown 32 having an angled lower end surface providing a piercing point 40.

The staples 30 are advanced by the cartridge 22 (FIG. 1) and applied to tissue. The stapler 20 is manipulated so the cartridge 22 is positioned adjacent the tissue to be stapled. The cartridge 22 is advanced farther to push the piercing points 40 of one staple 30 extending from the cartridge into the tissue so the points penetrate the tissue. The staple legs 38 may be advanced into the tissue to a predetermined depth depending on design parameters. In some applications, it may be desirable to advance the legs 38 into the tissue until the staple crown 32 engages the tissue and/or auxiliary element being stapled to the tissue. Once the legs 38 are advanced to the desired depth, the stapler 20 is actuated to deform the staple crown 32 so the staple legs 38 assume a generally closed configuration as illustrated in FIG. 3. In one embodiment, the pointed ends 40 of the staple leg 38 overlap as shown in FIG. 3.

In one embodiment of the cartridge 22, the staples 30 are stored in a side-by-side serial arrangement as illustrated in FIG. 4. The staples 30 are oriented so the staple legs 30 point generally downward and perpendicular to a longitudinal direction 42. The staples 30 are biased toward the forward end 26 of the stapler 20 by a helical compression spring 44 that forces an engaging member 46 against a last staple at a back end of the series of staples.

FIG. 4 schematically illustrates movement of staples 30 in the cartridge 22 (FIG. 1). When the stapler 20 is actuated to apply a staple 30, a lead staple at the front end of the series is pushed down an angled path (as schematically illustrated by arrow 50) and pivots about 90 degrees to the position generally indicated for the staple 30B. In this position, the staple legs 30 point forward. The staple 30B is pivoted by a guide track (not shown) and staple former 52 (partially shown). This causes the staple 30B to advance toward the forward end of the stapler 20 where the points 40 of the staple legs 30 penetrate the tissue. As the staple 30B advances farther, the staple crown 32 is bent around an anvil 54 so the staple legs overlap in a fastened configuration as illustrated in FIG. 4.

As shown in FIG. 1, the staples 30 are stored in the cartridge 22 adjacent the forward end 26 of the stapler 20. The cartridge 22 also has a generally circular transverse cross section. The diameter of the cartridge 22 is generally constant and between about 3 millimeter and about 15 millimeter. The cartridge 22 tapers at its forward end to a non-circular, flattened configuration as shown in FIG. 1. The cartridge 22 is mounted on the flexible shaft 24. In one embodiment, this shaft 24 is flexible along its entire length. The handle 28 includes a rotational control knob 60 for rotating the shaft 24 and cartridge 22 relative to the handle. In addition, the manipulator handle 28 includes a pivoting grip or trigger lever 62 that actuates the cartridge to advance the staple 30 and to apply it to tissue.

The cartridge 22 is removable from the forward end 26 of the stapler 20 so that when all of the staples 30 initially supplied in the cartridge have been applied to tissue, the empty cartridge may be removed from the stapler, and a new cartridge full of staples may be installed on the stapler.

The staples 30 are advanced in the cartridge 22 and applied to tissue by squeezing a trigger lever 62 on the manipulator handle 28. The trigger lever 62 is pivotally mounted on the handle 28 for pivotal movement in the rearward direction and in the forward direction as indicated by the double-headed arrow 64 in FIG. 1. The handle 28 also includes a grip 66 for receipt in the palm of the hand while the fingers of the hand extend around the trigger lever 62 to squeeze the trigger lever rearward toward the handle grip.

The components of the manipulator handle 28 may be fabricated from suitable materials. It is presently contemplated that some of the components, such as the knob 60, the trigger lever 62 and handle grip 66 may be fabricated from synthetic polymers, such as polycarbonate or nylon. It is also envisioned that suitable alternative materials may be used. For some of the other components, especially components that transfer internal forces and moments, metal materials (e.g., steel or stainless steel) may be used.

The flexible shaft 24 includes an outer flexible tube 70 as shown in FIG. 1. The rearward end of the tube 70 is connected to the rotational control knob 60 so the tube rotates with the control knob. In a presently contemplated embodiment, the tube 70 has a generally circular transverse cross section, an inner diameter of between about 1 millimeter and about 13 millimeter, and an outer diameter of between about 1.5 millimeter and about 15 millimeter. Further, the tube 70 has a length of between about 10 inches and about 100 inches. It is envisioned that the tube 70 may be coiled stainless steel or a synthetic polymer.

A flexible cable or linkage 72 extends through the tube 70. As will be explained in greater detail below, the cable 72 is operatively connected to the lever 62 and the cartridge 22 so that a staple 30 is advanced forward in the cartridge and applied to tissue with each squeeze of the lever.

Thus, as will be appreciated by those skilled in the art, the shaft 24 may be advanced into a patient. Once the cartridge 22 has been advanced to a position adjacent the tissue to be fastened, the cartridge may be rotated into an desired orientation by turning the knob 60. Once the cartridge 22 is oriented as desired, the trigger 62 is pulled to advance and apply a staple 30 to adjacent tissue.

Configuration and operation of the cartridge 22 is identical to that described in U.S. Pat. No. 5,588,581, which is hereby incorporated by reference in its entirety. Accordingly, the configuration and operation of the cartridge will not be described in detail. Likewise the internal configuration and operation of the control knob and lever 60, 62, respectively, are described in detail in U.S. Pat. No. 5,588,581 and will not be described further. As those skilled in the art will appreciate, the precise connections of the control knob and lever 60, 62 to the tube 70 and cable 72 may vary without departing from the scope of the present invention.

Figure 5:
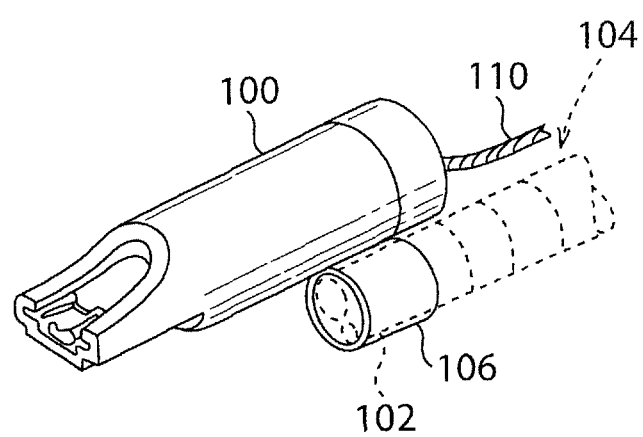
FIG. 5 is a perspective of a stapler of a second embodiment of the present invention.

In another embodiment of the present invention shown in FIG. 5, a cartridge 100 similar to that described above is mounted laterally adjacent a tip 102 of a conventional flexible endoscope, generally designated by 104, by means of a visually transparent cap 106 having an interference fit with the tip. An actuation cable 110 extends rearward beside the endoscope 104. The cable 110 includes a grip (not shown) at its end opposite the cartridge 100 for pulling the cable to actuate the cartridge advancing a staple 30 and applying it to tissue.

As will be further appreciated by those skilled in the art, the cartridges 22, 100 described above allow a surgeon to perform a method of approximating mucosa in a hollow body organ. The cartridge is positioned adjacent the tissue, and the cartridge is actuated to advance a staple 30 into position so its points 40 extend from the cartridge. In one embodiment, it is envisioned that the staple 30 may be partially deformed so the points 40 are slightly angled toward each other. The surgeon advances the cartridge, sticking one of the points into the mucosal tissue near one edge of the wound. The device is manipulated, such as with a remote steering device or in the case of the second embodiment by manipulating the endoscope, so that the opposite side of the wound is engaged by the opposite staple tip 40. The cartridge is then fully actuated to complete the staple formation. In so doing, the two edges of the wound are drawn together and into a position in which the wound is closed so healing can occur.

Mucosa in a hollow body organ may be approximated using another method. An flexible endoscope is placed in the hollow body organ, such as a stomach. For example, the endoscope is inserted through the esophagus and into the stomach. A guide wire is placed into the jejunum, using conventional guide wire techniques, and the endoscope is removed from the patient. A cartridge 22 is inserted into the patient, using the guide wire as an insertion guide. The endoscope is inserted into the patient following the shaft 24 of the stapler 20, and the guide wire is withdrawn. A conventional tissue grasping end effector or grasper is inserted through a working channel of the endoscope into the patient. The grasper is used to close the tissue near the inner edges of the mucosal wound to bring the edges into close approximation. Then the cartridge 22 is positioned over the approximated mucosal tissue edges. The trigger 62 of the stapler 20 is actuated to advance a staple 30 from the cartridge 22 and into the approximated edges. The trigger 62 is further actuated to close the staple 30, closing the wound and allowing healing to proceed.

Another method of using the device includes closing a full thickness wound such as a gastrotomy. The stapler may work in conjunction with an end effector intended for grasping or manipulating tissue, such as a grasper extending through a working channel of a conventional endoscope. The grasper extends from the end of the endoscope generally parallel to the stapler 100. In alternate embodiments, the tissue manipulating device may be a singe needle device formed as a corkscrew or a two needle device having curved needles extending in generally opposite directions. The tissue manipulating device is advanced and activated to engage the tissue near the full thickness wound. In one embodiment, the device is inserted into the wound so it engages both sides of the wound, fully through the thickness of the wound. The two edges are manipulated to bring the two edges close together. The cartridge 100 is actuated so a staple is deployed to secure the edges of the wound together. A plurality of staples 30 may be applied in this way to provide closure to the wound and to allow healing to proceed.

As will be appreciated by those skilled in the art, the devices described above permit a surgeon to complete mucosal resections and closures within the esophagus, stomach and colon. Further, wounds in the stomach may be repaired using a stapling device without making an incision. Tissue in the digestive tract may be approximated or remodeled without making an incision. Still further, tissue may be repaired in the abdominal cavity by making an incision in the gastric wall rather than in the abdominal wall. In addition, the offset cap attachment provided in the device 100 of the second embodiment allows visual confirmation of staple placement through the corresponding endoscope.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A surgical instrument for fastening tissue with a staple that is deformable from an open configuration in which tissue is initially engaged by ends of the staple to a fastened configuration in which the ends of the staple are moved toward each other so the staple closes around the tissue thereby fastening the tissue, said instrument comprising:
   a cartridge adapted for containing the staple, said cartridge including a mechanism adapted to selectively advance the staple toward a forward end of the cartridge so the ends of the staple protrude from the cartridge and to selectively close the staple, the cartridge further including a housing having an exterior surface;
   a mount connected to the exterior surface of the housing of the cartridge and adapted for mounting the cartridge to an end of an endoscope laterally offset from a tip of the endoscope so tissue can be viewed through the endoscope when fastened wherein the cartridge includes a longitudinal axis which is offset from the longitudinal axis of the endoscope and substantially aligned with a longitudinal axis of the mount;
   a linkage connected to the cartridge for actuating the mechanism to advance and close the staple; and
   a remote actuator connected to the linkage a predetermined distance from the cartridge for actuating the mechanism from a position remote from the cartridge.

2. A surgical instrument as set forth in claim 1 in combination with the endoscope.

3. A surgical instrument as set forth in claim 2 wherein the endoscope includes a selectively articulatable flexible shaft for guiding the cartridge into position in the patient.

4. A surgical instrument as set forth in claim 3 wherein the mount is selectively removable from the endoscope.

5. A surgical instrument as set forth in claim 2 wherein the mount includes a visually transparent cap shaped and dimensioned for selective attachment to the tip of the endoscope.

6. A surgical instrument as set forth in claim 5 wherein the longitudinal axis of the cartridge is offset from a longitudinal axis of the transparent cap.

7. A surgical instrument as set forth in claim 1 wherein:
   the staple is a first staple; and
   the cartridge is adapted for containing a plurality of staples including said first staple.

8. A surgical instrument as set forth in claim 7 wherein the plurality of staples are serially arranged in the cartridge.

9. A surgical instrument as set forth in claim 1 wherein the mount includes a visually transparent cap shaped and dimensioned for selective attachment to the tip of the endoscope.

10. A surgical instrument as set forth in claim 9 wherein the longitudinal axis of the cartridge is offset from a longitudinal axis of the transparent cap.

* * * * *